US010383640B2

(12) United States Patent
Houssiere et al.

(10) Patent No.: US 10,383,640 B2
(45) Date of Patent: Aug. 20, 2019

(54) SURGICAL DRILL

(71) Applicant: Interactive Neuroscience Center, LLC, New York City, NY (US)

(72) Inventors: Charles Houssiere, Houston, TX (US); Ashok Gowda, Houston, TX (US); Manish Ahuja, Houston, TX (US)

(73) Assignee: Innovate Our World Consultants, LLC, Houston, TX (US)

( * ) Notice: Subject to any disclaimer, the term of this patent is extended or adjusted under 35 U.S.C. 154(b) by 641 days.

(21) Appl. No.: 14/853,974

(22) Filed: Sep. 14, 2015

(65) Prior Publication Data

US 2016/0000448 A1 Jan. 7, 2016

Related U.S. Application Data

(63) Continuation of application No. PCT/US2014/030056, filed on Mar. 15, 2014.

(60) Provisional application No. 61/800,883, filed on Mar. 15, 2013, provisional application No. 61/915,302, filed on Dec. 12, 2013.

(51) Int. Cl.
| | |
|---|---|
| *A61B 34/20* | (2016.01) |
| *A61B 17/16* | (2006.01) |
| *A61B 17/17* | (2006.01) |
| *A61B 90/11* | (2016.01) |
| *A61B 90/00* | (2016.01) |

(52) U.S. Cl.
CPC ...... *A61B 17/1622* (2013.01); *A61B 17/1615* (2013.01); *A61B 17/1626* (2013.01); *A61B 17/1628* (2013.01); *A61B 17/1695* (2013.01); *A61B 17/1739* (2013.01); *A61B 34/20* (2016.02); *A61B 90/11* (2016.02); *A61B 2034/2055* (2016.02); *A61B 2090/3983* (2016.02)

(58) Field of Classification Search
CPC . A61B 34/20; A61B 17/1695; A61B 17/1615; A61B 17/1739; A61B 17/1628; A61B 17/1626
See application file for complete search history.

(56) References Cited

U.S. PATENT DOCUMENTS

2008/0097477 A1 * 4/2008 Wascher ................ A61B 90/36
606/130
2010/0114099 A1 * 5/2010 Patwardhan ....... A61B 17/1703
606/80

* cited by examiner

*Primary Examiner* — Richard G Louis
(74) *Attorney, Agent, or Firm* — Equip Law Group; Christopher Quan

(57) ABSTRACT

This invention is directed to devices and methods for surgical access to the body, and particularly to surgical drills for accessing a body cavity and methods therefor. In general, a surgical drill is utilized to gain access to a body cavity or part, such as where bone and/or other hard tissues need to be pierced. For example, the skull and other bones with internal cavities may require surgical access to treat body portions contained within the bone. Further in general, it may be generally desirable to create access holes or openings which may be as small as possible and at a particular direction and/or trajectory. In this manner the access hole or opening may be utilized to guide another device, such as a treatment device, to a particular target along the established trajectory of the access hole or opening.

5 Claims, 3 Drawing Sheets

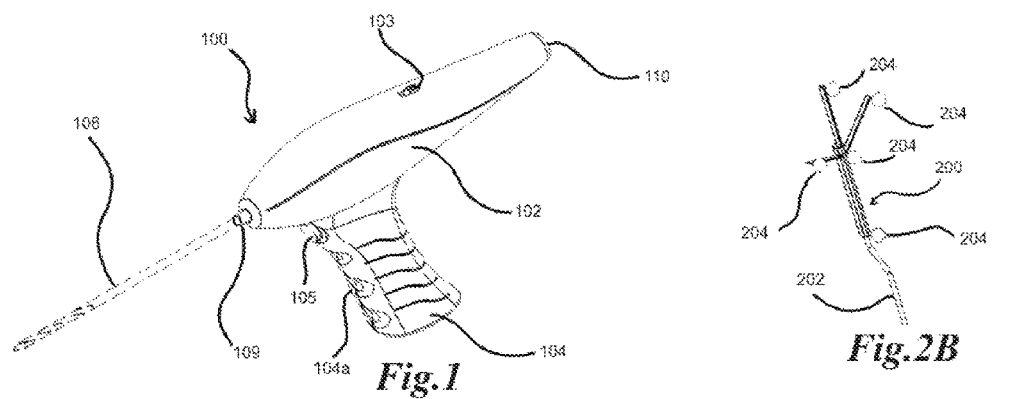
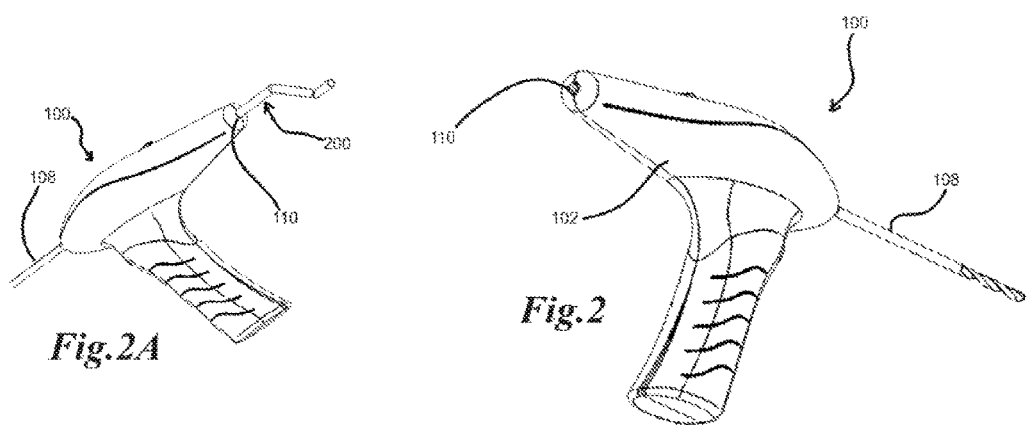
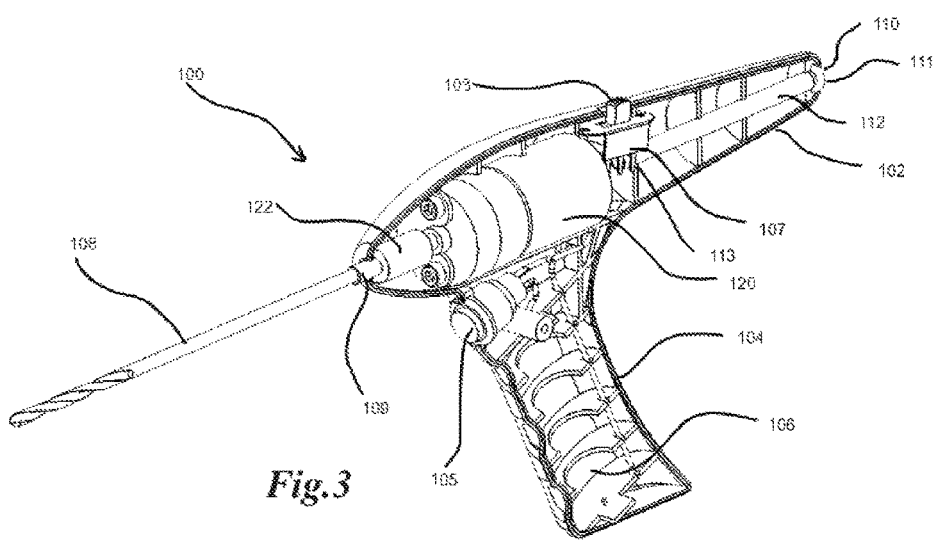

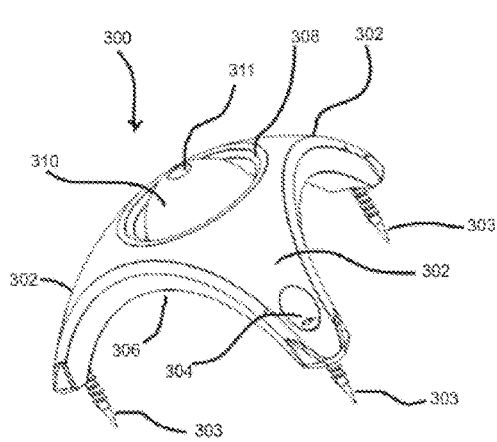
*Fig.4*
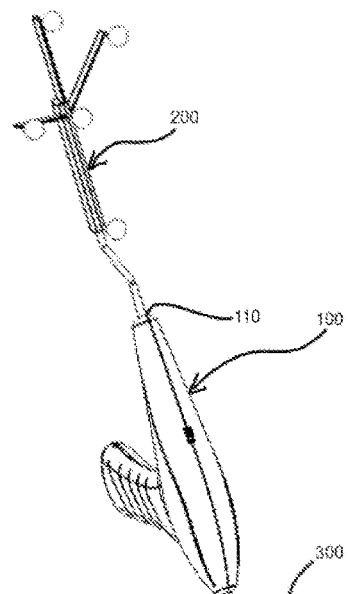
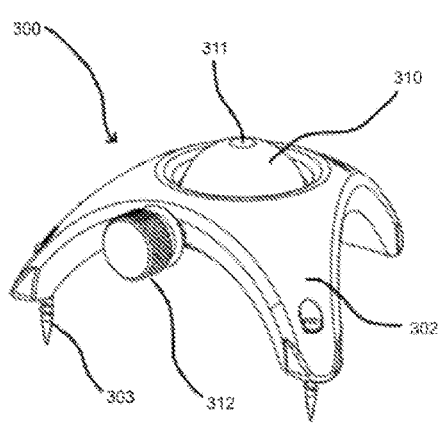
*Fig.4B*
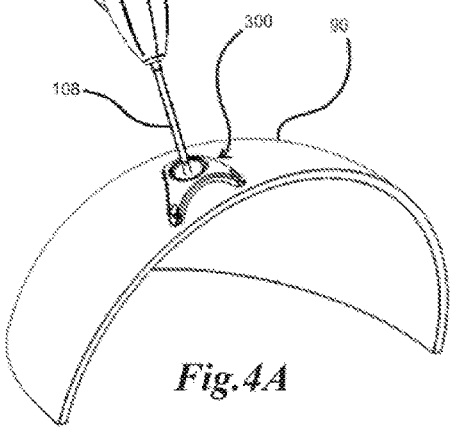
*Fig.4A*
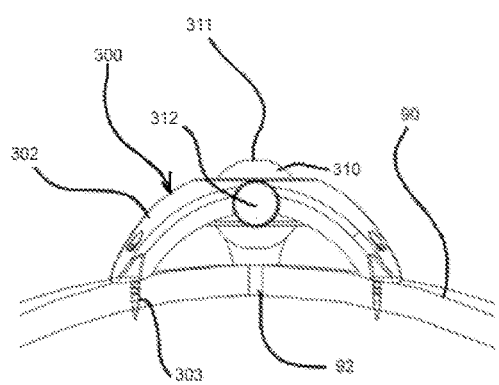
*Fig.4C*

SURGICAL DRILL

CROSS-REFERENCE TO RELATED APPLICATIONS

This application is a continuation of PCT International Application Ser. No. PCT/US14/30056, filed Mar. 15, 2014, entitled "SURGICAL DRILL", which claims the benefit and priority of U.S. provisional patent application Ser. No. 61/800,883, filed Mar. 15, 2013, entitled "SURGICAL DRILL", and Ser. No. 61/915,302, filed Dec. 12, 2013, entitled "SURGICAL DRILL", the contents of all of which are hereby incorporated by reference in their entireties.

FIELD OF THE INVENTION

This invention relates to devices and methods for surgical access to the body, and particularly to surgical drills for accessing a body cavity and methods therefor.

BACKGROUND OF THE INVENTION

Stereotactic head frames have a long and proven history in neurosurgery. The two most commonly used are the Leksell (Elekta) and CRW (Integra Neurosciences) frames. In these procedures, a frame is mounted to the head by screwing pins directly against the patient's skull for fixation at four points. The head with attached frame are then imaged by CT or MRI to identify targets, either manually or more frequently with computerized software, in relation to the external frame. Since both the frame and target can be viewed on the images, the distance of the target from given reference points on the frame can be measured in three coordinates. Next in the OR, an arc apparatus is attached to the head frame and adjusted based on the previously measured coordinates and desired trajectory. One in position, a guide is used to drill a hole along a trajectory to the target. These head frames are associated with high accuracy (1-2 mm) for reaching target structures, much of which is achieved by having a permanent fixation between the skull and guide being used for creating the cranial access. Unfortunately, the frame is cumbersome, uncomfortable for patients, and time intensive.

Frameless stereotactic procedures rely on registration of the patient's skull using anatomical landmarks, skin fiducial, or bone fiducials to a pre-acquired MRI or CT scan. In the operating room the orientation of fiducial markers or skin surfaces is registered using stereoscopic cameras on the navigation system to a volume of brain images. Once registration is completed, the navigation system can show the relationship of any registered surgical instruments to patient's brain anatomy. The two major manufacturers of these neuronavigation systems are Medtronic and Brainlabs. Both companies offer accessories which attach to the patients bed to allow twist drill access to a target along a defined trajectory. The drawback to these accessories (Medtronic-Precision Aiming Device and Brainlab Varioguide) are that neither is directly attached to the patient's head, and therefore any movement of the drill is not directly accompanied by a corresponding movement of the head. Both systems require additional time and resource to set up in the operating room. Finally, because skin fiducials are movable in relation to the underlying skull, additional error may be realized from the registration alone.

SUMMARY OF THE INVENTION

This invention is directed to devices and methods for surgical access to the body, and particularly to surgical drills which may be stereotactically guided to a predetermined trajectory to access a body cavity and methods therefor. In general, a surgical drill is utilized to gain access to a body cavity or part, such as where bone and/or other hard tissues need to be pierced. For example, the skull and other bones with internal cavities may require surgical access to treat body portions contained within the bone. Further in general, it may be generally desirable to create access holes or openings which may be as small as possible and at a particular direction and/or trajectory. In this manner the access hole or opening may be utilized to guide another device, such as a treatment device, to a particular target along the established trajectory of the access hole or opening. Also in general, it may be desirable for portions or the entirety of the surgical drill to be sterilizable for use in surgical procedures, such as by autoclave. It may further be generally desirable for the surgical drill to be disposable, small, to require minimal assembly for use, and to be as powerful as possible to gain access, such as through bone, as quickly and efficiently as possible.

In an exemplary aspect of the invention, a surgical drill of the present invention may generally include a main body, and a mounting feature towards one end of the main body adapted for mounting a drill bit. A channel or cannulation inside the main body is adapted for receiving a navigation device in a fixed orientation relative to said drill bit. The channel or cannulation may extend partially through the inside of the main body. In one aspect, the drill bit may be removably mounted to the mounting feature. In another aspect, the drill bit may be permanently mounted to the mounting feature. The handle may aid in providing for simple and precise use during a surgical procedure.

The navigation device may include a stereotactic tracking feature, for example a navigation probe or wand, or tracking equipment, for stereotactically tracking and controlling the trajectory of the surgical drill during use such that, for example, an access hole may be drilled along a particular trajectory, such as towards a particular target, guided by the tracking feature. In one aspect, the navigation device may be received into the channel or cannulation and be substantially disposed inside the main body of the surgical drill. In another aspect, the navigation device may be mounted to the channel or cannulation through an adaptor and be substantially disposed outside the main body of the surgical drill. In a further aspect, the navigation device may be received into the channel or cannulation and be mounted substantially inside the main body of the surgical drill. For example, the surgical drill may generally be compatible and/or be compatible via adapters to receive a standard navigation probe or wand and/or other tracking equipment used in stereotactic surgery. In general, the channel or partial cannulation may be relatively deep in relation to the insertable probe or wand, as this may aid in stability and accuracy of tracking. The channel or partial cannulation may also be adapted for fitting insertable probes, wands or devices of different diameters without the use of an adapter, sleeve or shim, such as, for example, by including at least a tapering portion, a portion having different diameters, such as a stepped portion, and/or a combination thereof. The channel or partial cannulation may also include a locking and/or other retaining feature such that an inserted probe, wand or device may be securely retained in the channel or partial cannulation. The locking and/or other retaining feature may also be adapted to aid in retention of the inserted probe, wand or device, but may, for example, allow free rotation of the inserted probe, wand or device in the channel or partial cannulation. In some embodiments, the channel or partial cannulation may also be in direct line with the drill bit such that the orientation of the inserted probe or wand matches the trajectory of the drill bit and thus the drilled access hole. In general, it may be desirable for the channel or partial cannulation not to pass through the entire drill such that the sterility of the channel or partial cannulation may be separately maintained from the sterility of the drill bit end of the surgical drill.

In another embodiment, the surgical drill itself may include features that enable the tracking of the position and/or orientation of the surgical drill, such as navigation fiducials which may be built in or removable.

In one aspect of the invention, a surgical drill may generally include a main body with a handle for simple and precise use during a surgical procedure. The main body and/or handle may generally include a motor, a power source, a control system for the motor and/or gearing mechanisms for the output of the motor. A drill bit and/or other tool may be generally attached to the drill, such as reversibly by a chuck, or permanently by direct attachment to a gearing mechanism or to the motor, and may extend from one end of the main body. In some embodiments, the drill bit may be permanently mounted to the motor and/or to a gearing mechanism, such that the drill bit may not be removed from the surgical drill. This may be utilized to make the surgical drill more resistant to user error, such as, for example, by preventing the wrong type of drill bit from being used, and/or make the surgical drill simplified in construction and/or more disposable. The surgical drill may further include an actuator, such as a trigger or other appropriate control, for actuating the motor and the attached drill bit. The actuator may be present on the outside of the surgical drill, such as at the handle or other portion of the main body, or other controls may be utilized, such as wired controls, wireless controls, voice control, and/or other appropriate control mechanism. In some embodiments, the power source may be non-rechargeable and/or non-removable. This may be utilized to make the surgical drill more disposable and/or to prevent the surgical drill from being utilized past its intended life. For example, the power source may hold a known, finite charge, which may be selected to match a given expected usage life for the surgical drill.

In another aspect of the invention, the surgical drill may be utilized with a stereotactic access device.

In general, a stereotactic device may include portions or features for fixing the device to a portion of a patient's body, such as, for example, a skull, such that the device may be generally spatially fixed in relation to the patient's body or part thereof. The stereotactic device may also generally include portions or features for guiding a medical device or other device at a particular trajectory in relation to the patient's body or part thereof.

In one aspect, a stereotactic access device includes a plurality of mounting arms which may further include mounting devices or features such that, for example, the stereotactic access device may be mounted securely to a patient's body or part thereof. In some embodiments, the mounting arms may generally be adapted to provide a stable mounting of the stereotactic access device to a patient's body or part thereof. For example, many body parts have curved or irregular surfaces such that stable mounting may be desirable. In an exemplary embodiment, the mounting arms may form at least a stable plane such that when the mounting arms are attached to the patient's body, the stereotactic access device may generally be spatially stable and/or attached securely. In one embodiment, the stereotactic access device may include three mounting arms which may form a stable plane. The mounting arms may also be adapted to conform to the contours of a patient's body or part thereof, such as, for example, a skull. The mounting arms may further be adapted to contour, for example, such that there may be access space between the stereotactic access device and the patient's body and/or portion thereof. This may be desirable, for example, to manipulate a medical device and/or other device between the stereotactic access device and the patient's body and/or portion thereof.

In another aspect, a stereotactic access device includes a mounting and/or guiding feature such that a medical device and/or other device may be mounted to or guided to the stereotactic access device such that, for example, the device may be retained at a particular orientation and/or spatial relationship to the patient's body or part thereof. In some embodiments, the mounting and/or guiding feature may include a rotatable portion, such as an orbitally rotatable and/or swivelable portion, such that the orientation of the portion may be changed with respect to the patient's body, a portion thereof, and/or the rest of the stereotactic access device. In an exemplary embodiment, the mounting and/or guiding feature may include, for example, a rotating sphere which may further include a guide channel to, for example, receive a medical device and/or other device.

In a further aspect, a stereotactic access device includes features for aiding in mounting, positioning and/or registering the position and/or orientation of the stereotactic access device, for example, in relation to the patient's body and/or portion thereof. In some embodiments, the stereotactic access device may include, for example, mounting hardware such as, for example, screws, nails, bolts, pins, and/or any other appropriate mounting hardware or combination thereof. For certain curvatures and/or shapes of a body and/or portion thereof, spacers and/or other adjustment accessories, such as spacers between the end of the mounting arm(s) and the body, may be utilized such that a stable plane may be established with the stereotactic access device. In general, the mounting hardware may provide, for example, stable and/or secure retention and/or fixation of the stereotactic access device to a patient's body and/or portion thereof, such as, for example, to a bone or soft tissue via, for example, mounting arms. In some embodiments, the mounting hardware may also provide and/or act as, for example, fiducial markers for aiding in positioning and/or registering the position and/or orientation of the stereotactic access device, such as, for example, relative to the patient's body and/or portion thereof. For example, the mounting hardware may be registered and/or imaged by a detection modality, such as, for example, magnetic resonance imaging (MRI), X-ray, computerized tomography (CT), ultrasound, and/or any other appropriate detection modality or combination thereof.

Reusable and/or rechargeable surgical drills are useful and may be desirable in certain uses. In general, surgical drills are made of expensive components as all of the components are sterilizable components and is thus not economical to dispose of them after one, or even a few uses. The drills are also generally constructed such that the drill bits are mounted and replaced by the operator(s). However, for some delicate operations, it is not desirable to have a drill that may stop working in the middle of a drilling operation, for example, due to part failure because of wear or harsh sterilization process used, due to operator errors during assembly or replacement or the drill bit, or due to failure of rechargeable batteries.

In a further exemplary aspect of the invention, a surgical drill of the present invention may generally include a main body, and a drill bit permanently mounted towards one end of the main body. A channel or cannulation inside the main body is adapted for receiving a navigation device in a fixed orientation relative to said drill bit. The channel or cannulation may extend partially through the inside of the main body. The drill bit may be mounted to a mounting feature present on the main body or it may be an extension of the main body.

In one aspect, the surgical drill of the present invention may be manufactured from materials which may not be sterilized by certain methods, such as, for example, by autoclave, such that it may not be reused. In another aspect, the surgical drill of the present invention may include a power source of the disposable surgical drill to be non-rechargeable and/or non-removable such that the disposable surgical drill may only be used for a finite period of time. It may generally be desirable for the surgical drill to be disposable to, for example, prevent reuse, prevent use in excess of its design life, decrease the chance of cross-contamination, and/or to simplify and/or decrease the cost of the design. In a further example, it may generally be desirable to have a surgical drill that may require minimal assembly to minimize operator error.

The further exemplary aspect of the invention of the drill may include all the aspects and features discussed above for all the other exemplary aspects of the invention.

In another aspect, a stereotactic access device is utilized in methods for accessing the interior of a patient's body at a particular location and/or along a particular trajectory. In an exemplary embodiment, a method for stereotactic access may include:

Step 1: After registration of the patient and navigation tools, a standard navigation wand may be inserted into a channel of a surgical drill, which is used to determine and mark a rough entry point, and the patient may then be prepped. The drill bit may then be inserted into the sphere of the stereotactic access device such that the surgeon may hold both devices, for example, with one hand.

Step 2: Using stereotactic navigation software, the surgeon may find the desired entry point again and may then align the navigation wand and the coupled surgical drill with the planned trajectory to a target. The surgeon may then slide the stereotactic access device down onto the patient's body and mounting hardware, such as, for example, three small titanium screws, may then be secured, for example, through the skin and into bone, such as, for example, the skull. The wand may be used again to confirm the trajectory, such as prior to locking the device in place.

Step 3: A stab incision may also be made at the entry site under the stereotactic access device. The surgeon may then drill a hole through, for example, a bone such as the skull, with the drill bit locked onto the trajectory by the stereotactic access device and tracked with the coupled navigation wand.

Step 4: The drill may then be retracted to optionally allow, for example, a bone screw or anchor to be placed under the stereotactic access device. The drill adapter may be made to fit into the bone screw or anchor's proximal end such that the threads of the screw may fall into the hole created in step 3. A biopsy probe may also be passed directly through an appropriate adapter, for example, such as with its own thumb screw, and may be used to acquire, for example, tissue samples.

Step 5: For placement of probes or electrodes, the surgeon may secure the bone screw by securing it in, for example, the previously drilled hole.

Step 6: The stereotactic access device may be removed, for example, by unscrewing the three screws, and if any stab incisions were created, they may be closed using a single staple or suture. A Touhy-Borst adapter may also be threaded onto the proximal female luer of the bone screw, which may allow applicators to pass through while ensuring a sterile field.

In some embodiments, the stereotactic access device may also be left in place after a hole is drilled. For example, a bone screw may connect to the stereotactic access device such that a continuous sealed channel may be established from the stereotactic access device through the bone screw and into the body. A sealing cap and/or other sealing component may also be included to close off the introducing end of the stereotactic access device.

In other embodiments, the stereotactic access device may be left in place and an introducer may be inserted into the channel of the stereotactic access device and into the drilled hole in the body. The end of the introducer may further include a cap and/or a seal such that the channel may be kept sterile.

In some aspects, the stereotactic access device may be desirable as it may generally be utilized with existing and/or standard practice navigation devices, probes and/or systems, and may thus be adaptable to a diverse number of medical practices with very little additional training and/or the need for specialized equipment. For example, the stereotactic access device may generally be compatible and/or be compatible via adapters to receive a standard navigation probe or wand, treatment devices, drills and/or other equipment used in stereotactic surgery. Further, use of the stereotactic access device may generally be intuitive and aid in surgical usage with a minimal number of moving parts and/or components such that, for example, users may use the stereotactic access device with minimal difficulty, while still being highly versatile in application due to a universal use design.

The present invention together with the above and other advantages may best be understood from the following detailed description of the embodiments of the invention illustrated in the drawings.

BRIEF DESCRIPTION OF THE FIGURES

FIGS. 1 and 2 illustrate a surgical drill in an embodiment of the present invention;

FIG. 2A illustrates a navigation wand mounted in a surgical drill;

FIG. 2B illustrates an example of a navigation wand;

FIG. 3 illustrates a partial cutaway of a surgical drill;

FIGS. 4, 4B and 4C illustrate a stereotactic access device in some embodiments of the present invention;

FIG. 4A illustrates a surgical drill with a stereotactic access device and a navigation wand;

DETAILED DESCRIPTION OF THE INVENTION

Figure 5:
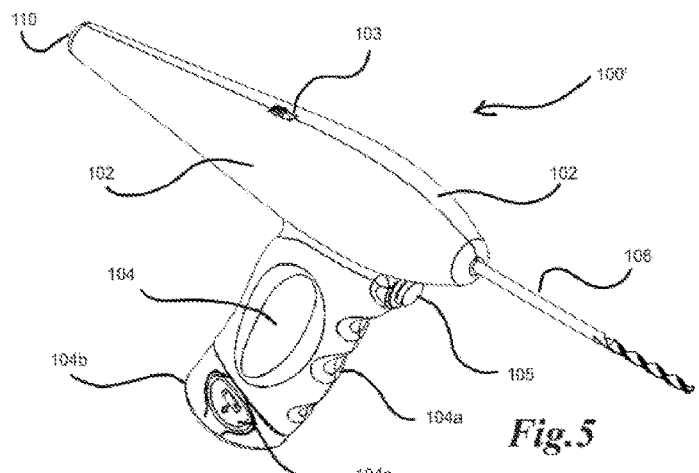
FIG. 5 illustrates another embodiment of a surgical drill.

The detailed description set forth below is intended as a description of the presently exemplified devices, methods and materials provided in accordance with aspects of the present invention, and it is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

This invention is directed to devices and methods for surgical access to the body, and particularly to surgical drills for accessing a body cavity and methods therefor. In general, a surgical drill is utilized to gain access to a body cavity or part, such as where bone and/or other hard tissues need to be pierced. For example, the skull and other bones with internal cavities may require surgical access to treat body portions contained within the bone. Further in general, it may be generally desirable to create access holes or openings which may be as small as possible and at a particular direction and/or trajectory. In this manner the access hole or opening may be utilized to guide another device, such as a treatment device, to a particular target along the established trajectory of the access hole or opening. Also in general, it may be desirable for portions or the entirety of the surgical drill to be sterilizable for use in surgical procedures, such as by autoclave. It may further be generally desirable for the surgical drill to be disposable, small, to require minimal assembly for use, and to be as powerful as possible to gain access, such as through bone, as quickly and efficiently as possible. For example, it may be desirable for the surgical drill to be manufactured from materials which may not be sterilized by certain methods, such as, for example, by autoclave, such that it may not be reused. In another example, it may be desirable for the power source of the disposable surgical drill to be non-rechargeable and/or non-removable such that the disposable surgical drill may only be used for a finite period of time. It may generally be desirable for the surgical drill to be disposable to, for example, prevent reuse, prevent use in excess of its design life, decrease the chance of cross-contamination, and/or to simplify and/or decrease the cost of the design.

In one aspect of the invention, a surgical drill, such as the surgical drill 100 in FIG. 1, may generally include a main body 102 with a handle 104 for simple and precise use during a surgical procedure. The handle 104 may also include gripping features for better handling and ergonomics, such as ergonomic grip 104a as illustrated. The main body 102 and/or handle 104 may generally contain a motor, a power source, a control system for the motor and/or gearing mechanisms for the output of the motor, as shown and discussed further below in relation to FIG. 3. A drill bit and/or other tool, such as the drill bit 108 as illustrated in FIG. 1, may be generally attached to the drill 100 through a mounting 109, such as reversibly by a chuck, or permanently by direct attachment to a gearing mechanism or to the motor, and may extend from one end of the main body 102 as illustrated. The surgical drill 100 may further include an actuator, such as a trigger 105 or other appropriate control, for actuating the motor and the attached drill bit 108. The actuator may be present on the outside of the surgical drill 100, such as the trigger 105 is shown at the handle 104, or other portion of the main body 102, or other controls may be utilized, such as wired controls, wireless controls and/or other appropriate control mechanism. For example, foot pedals or other remote controls which may be common and familiar to surgeons may also be utilized.

As illustrated in FIG. 3, a motor 120 may couple to drill bit 108, which may be mounted at mounting 109. A gearing or other speed control mechanism may also be utilized, as illustrated with mechanism 122 between the motor 120 and the mounting 109. In some embodiments, the drill bit 108 may be permanently mounted to the motor 120 and/or to a gearing mechanism 122, such that the drill bit 108 may not be removed from the surgical drill 100. This may be utilized to make the surgical drill 108 more resistant to user error, such as, for example, by preventing the wrong type of drill bit from being used, and/or make the surgical drill 108 simplified in construction and/or more disposable. A reverse/forward control 103 may also be utilized to control the direction of the motor 120 via a circuit 107, with one setting for drilling and one setting for retracting. A battery or other power source may further be housed inside the surgical drill 100, such as in space 106 in the handle 104, such as with the batteries 106a illustrated in the surgical drill 100' of FIG. 5A. The batteries 106a may also be accessed by an opening, such as the access cap 104b, which may be actuated by release feature 104c as illustrated in FIG. 5. In some embodiments, the access cap 104b may be closed permanently such as to prevent the batteries 106a from being removed. This may be utilized to make the surgical drill 100 more disposable and/or to prevent the surgical drill 100 from being utilized past its intended life. For example, the batteries 106a may hold a known, finite charge, which may be selected to match a given expected usage life for the surgical drill 100.

An example of a motor which may be utilized includes one that may provide sufficient power/torque for drilling bone, while still being compact enough to fit in a handheld surgical drill 100 and be tolerant of sterilization conditions of the assembled surgical drill 100, such as:

Motor Type: Brushed DC Motor (with gear box)
Motor Manufacturer: LDO Motors Co., Ltd
Rated Voltage: 6 V DC
No Load Speed: 900 RPM+/−10%
No Load Current Draw: 0.6 A (1.2 A max)
Rated Torque: 0.4 kg·cm
Current at rated torque: 1.4 A (2.1 A max)
Speed at rated torque: 650 rpm+/−10%
Motor Diameter: 25 mm
Motor Length (excluding shaft): 49.8 mm
Motor Length (including shaft): 62.8 mm In an exemplary aspect of the invention, a surgical drill 100 may generally include a stereotactic tracking feature. In general, a stereotactic feature may be utilized to track and control the trajectory of the surgical drill during use such that, for example, an access hole may be drilled along a particular trajectory, such as towards a particular target. In one embodiment, as illustrated in FIGS. 1, 2 and 2A, the surgical drill 100 may include a channel or partial cannulation, such as channel 110, which may be used to mount a stereotactic guide, such as shown with wand 200 in FIG. 2A. For example, the surgical drill 100 may generally be compatible and/or be compatible via adapters to receive a standard navigation probe or wand and/or other tracking equipment used in stereotactic surgery, an example of which is shown with navigation wand 200 with a main wand portion 202 for inserting, and tracking fiducial markers shown as balls 204 in FIG. 2B. In general, the channel or partial cannulation may be relatively deep in relation to the insertable probe or wand, as this may aid in stability and accuracy of tracking FIG. 3 illustrates the channel 110 extending through a significant portion of the body 102 with interior portion 112. The channel or partial cannulation may also include a locking and/or other retaining feature such that an inserted probe, wand or device may be securely retained in the channel or partial cannulation, such as shown with the sealing ring 111 in FIG. 3. In some embodiments, the channel or partial cannulation may also be in direct line with the drill bit, as can be seen with channel 110 and drill bit 108 in FIG. 3, such that the orientation of the inserted probe or wand matches the trajectory of the drill bit and thus the drilled access hole. In general, it may be desirable for the channel or partial cannulation not to pass through the entire drill such that the sterility of the channel or partial cannulation may be separately maintained from the sterility of the drill bit end of the surgical drill. As illustrated in FIG. 3, the interior portion 112 of channel 110 ends at stop 113 and is separated from the drill bit 108.

The channel or partial cannulation may also be adapted for fitting insertable probes, wands or devices of different diameters without the use of an adapter, sleeve or shim, such as, for example, by including at least a tapering portion, a portion having different diameters, such as a stepped portion, and/or combinations thereof. The stepped portion may, for example, include multiple sections of different diameters which may, for further example, correspond to standard and/or common diameters for insertable probes, wands or devices. The channel or partial cannulation may also include sections with different cross-sections to accommodate different insertable probes, wands or devices, such as, for example, circular, square, triangular and/or any other cross-sectional shape which may be necessary.

Figure 5A:
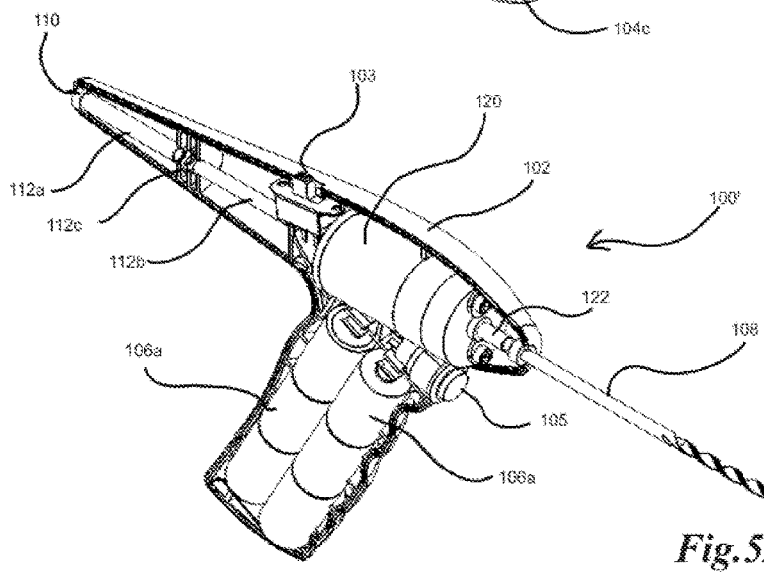
FIGS. 5A and 5B illustrate the internal components of a surgical drill with a variable diameter cannulation.

FIGS. 5 and 5A illustrate an example of a surgical drill 100' which may include a varying diameter channel or partial cannulation. FIG. 5A shows a multiple part channel 110 with sections 112a, 112b, which may be of different diameters for accommodating different sized probes, wands or devices, as seen with the varied diameters shown in FIG. 5B. The multiple part channel 110 may also include additional sealing rings, such as the ring 112c disposed between sections 112a, 112b, as illustrated.

Figure 5C:
FIGS. 5C and 5D illustrate examples of variable diameter cannulations.
Figure 5B:
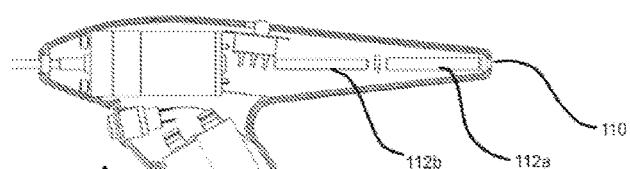
Figure 5D:
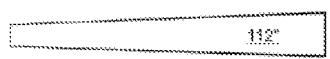

FIGS. 5C and 5D illustrate further examples of a channel 110 which may include a multiple stepped portion, such as the 3-step portion 112' shown in FIG. 5C, or a tapering portion 112" shown in FIG. 5D.

In general, any multiple portions or sections of the channel 110 may share a common center in the surgical drill 100', such that different insertable probes, wands or devices may be consistently positioned in the surgical drill, such as along the center line of the drill bit 108, to help ensure proper alignment and orientation determinations.

In another embodiment, the surgical drill itself may include features that enable the tracking of the position and/or orientation of the surgical drill, such as navigation fiducials which may be built in or removable.

In another aspect of the invention, the surgical drill may be utilized with a stereotactic access device.

In general, a stereotactic device may include portions or features for fixing the device to a portion of a patient's body, such as, for example, a skull, such that the device may be generally spatially fixed in relation to the patient's body or part thereof. The stereotactic device may also generally include portions or features for guiding a medical device or other device at a particular trajectory in relation to the patient's body or part thereof.

In one aspect, a stereotactic access device includes a plurality of mounting arms which may further include mounting devices or features such that, for example, the stereotactic access device may be mounted securely to a patient's body or part thereof. In some embodiments, the mounting arms may generally be adapted to provide a stable mounting of the stereotactic access device to a patient's body or part thereof. For example, many body parts have curved or irregular surfaces such that stable mounting may be desirable. In an exemplary embodiment, the mounting arms may form at least a stable plane such that when the mounting arms are attached to the patient's body, the stereotactic access device may generally be spatially stable and/or attached securely. In one embodiment, the stereotactic access device may include three mounting arms which may form a stable plane. The mounting arms may also be adapted to conform to the contours of a patient's body or part thereof, such as, for example, a skull. The mounting arms may further be adapted to contour, for example, such that there may be access space between the stereotactic access device and the patient's body and/or portion thereof. This may be desirable, for example, to manipulate a medical device and/or other device between the stereotactic access device and the patient's body and/or portion thereof.

FIG. 4 illustrates an example of an embodiment of a stereotactic access device 300. In some embodiments, such as illustrated, the stereotactic access device 300 may generally be a tripod and may include mounting arms 302, such as the three illustrated, which may provide a stable planar platform when mounted to a patient's body. The mounting arms 302 may also generally form a space 306 between the stereotactic access device 300 and a patient's body. This may be desirable such that the area may be freely accessed when the stereotactic access device 300 is in place on the patient's body.

In another aspect, a stereotactic access device includes a mounting and/or guiding feature such that a medical device and/or other device may be mounted to or guided to the stereotactic access device such that, for example, the device may be retained at a particular orientation and/or spatial relationship to the patient's body or part thereof. In some embodiments, the mounting and/or guiding feature may include rotatable portion such that the orientation of the portion may be changed with respect to the patient's body, a portion thereof, and/or the rest of the stereotactic access device. In an exemplary embodiment, the mounting and/or guiding feature may include, for example, a rotating sphere which may further include a guide channel to, for example, receive a medical device and/or other device.

In FIG. 4, the stereotactic access device 300 may include a mounting ball 310, which may be retained in track 308. The mounting ball 310 may generally rotate in the track 308 such that the guide channel 311 may be aligned at the appropriate angle, such as illustrated in FIG. 4A. The mounting ball 310 may thus retain another device, such as, for example, the drill bit 108 of surgical drill 100 with a coupled navigation wand 200, relative to the patient's body 90, such as illustrated in FIG. 4A. The mounting ball 310 may also include a securing part or feature, such as, for example, a securing screw, such that the mounting ball 310 may be locked in a particular orientation, such as with the thumbscrew 312 illustrated in FIGS. 4B and 4C.

In a further aspect, a stereotactic access device includes features for aiding in mounting, positioning and/or registering the position and/or orientation of the stereotactic access device, for example, in relation to the patient's body and/or portion thereof. In some embodiments, the stereotactic access device may include, for example, mounting hardware such as, for example, screws, nails, bolts, pins, and/or any other appropriate mounting hardware or combination thereof. For certain curvatures and/or shapes of a body and/or portion thereof, spacers and/or other adjustment accessories, such as spacers between the end of the mounting arm(s) and the body, may be utilized such that a stable plane may be established with the stereotactic access device. In general, the mounting hardware may provide, for example, stable and/or secure retention and/or fixation of the stereotactic access device to a patient's body and/or portion thereof, such as, for example, to a bone or soft tissue via, for example, mounting arms. In some embodiments, the mounting hardware may also provide and/or act as, for example, fiducial markers for aiding in positioning and/or registering the position and/or orientation of the stereotactic access device, such as, for example, relative to the patient's body and/or portion thereof. For example, the mounting hardware may be registered and/or imaged by a detection modality, such as, for example, magnetic resonance imaging (MRI), X-ray, computerized tomography (CT), ultrasound, and/or any other appropriate detection modality or combination thereof.

As illustrated in FIG. 4, the stereotactic access device 300 may include, for example, screws 303, which may be mounted at the ends of the mounting arms 302. The screws 303 may be, for example, self-tapping such that they may, for example, thread themselves into a surface, such as the patient's body. The screws 303 may also act as fiducials, as discussed above. For certain curvatures of the body and/or other situations requiring adjustment of the apparent dimensions of the mounting arms 302, spacers may be included, such as, for example, about the screws 303 between the end of the mounting arms 302 and the body, such that they may, for further example, effectively lengthen the mounting arms 302.

In another aspect, a stereotactic access device is utilized in methods for accessing the interior of a patient's body at a particular location and/or along a particular trajectory. In an exemplary embodiment, a method for stereotactic access may include:

Step 1: After registration of the patient and navigation tools, a standard navigation wand may be inserted into a channel of a surgical drill, which is used to determine and mark a rough entry point, and the patient may then be prepped. The drill bit may then be inserted into the sphere of the stereotactic access device such that the surgeon may hold both devices, for example, with one hand.

Step 2: Using stereotactic navigation software, the surgeon may find the desired entry point again and may then align the navigation wand and the coupled surgical drill with the planned trajectory to a target. The surgeon may then slide the stereotactic access device down onto the patient's body and mounting hardware, such as, for example, three small titanium screws, may then be secured, for example, through the skin and into bone, such as, for example, the skull. The wand may be used again to confirm the trajectory, such as prior to locking the device in place.

Step 3: A stab incision may also be made at the entry site under the stereotactic access device. The surgeon may then drill a hole through, for example, a bone such as the skull, with the drill bit locked onto the trajectory by the stereotactic access device and tracked with the coupled navigation wand.

Step 4: The drill may then be retracted to optionally allow, for example, a bone screw or anchor to be placed under the stereotactic access device. The drill adapter may be made to fit into the bone screw or anchor's proximal end such that the threads of the screw may fall into the hole created in step 3. A biopsy probe may also be passed directly through an appropriate adapter, for example, such as with its own thumb screw, and may be used to acquire, for example, tissue samples.

Step 5: For placement of probes or electrodes, the surgeon may secure the bone screw by securing it in, for example, the previously drilled hole.

Step 6: The stereotactic access device may be removed, for example, by unscrewing the three screws, and if any stab incisions were created, they may be closed using a single staple or suture. A Touhy-Borst adapter may also be threaded onto the proximal female luer of the bone screw, which may allow applicators to pass through while ensuring a sterile field.

In some embodiments, the stereotactic access device may also be left in place after a hole is drilled. For example, a bone screw may connect to the stereotactic access device such that a continuous sealed channel may be established from the stereotactic access device through the bone screw and into the body. A sealing cap and/or other sealing component may also be included to close off the introducing end of the stereotactic access device.

In other embodiments, the stereotactic access device may be left in place and an introducer may be inserted into the channel of the stereotactic access device and into the drilled hole in the body. The end of the introducer may further include a cap and/or a seal such that the channel may be kept sterile.

In some aspects, the stereotactic access device may be desirable as it may generally be utilized with existing and/or standard practice navigation devices, probes and/or systems, and may thus be adaptable to a diverse number of medical practices with very little additional training and/or the need for specialized equipment. For example, the stereotactic access device may generally be compatible and/or be compatible via adapters to receive a standard navigation probe or wand, treatment devices, drills and/or other equipment used in stereotactic surgery. Further, use of the stereotactic access device may generally be intuitive and aid in surgical usage with a minimal number of moving parts and/or components such that, for example, users may use the stereotactic access device with minimal difficulty, while still being highly versatile in application due to a universal use design.

It will be appreciated by those of ordinary skill in the art that the present invention can be embodied in other specific forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

The invention claimed is:

1. A method for stereotactic access to a body cavity comprising:
    providing a surgical drill comprising:
        a main body having a mounting feature adapted for reversibly mounting a drill bit towards one end of the main body;
        a handle portion disposed substantially toward said one end of the main body; and
        a channel inside said main body comprising a sealing ring, said channel extending partially through said inside of said main body in an elongated portion extending significantly further rearward from said handle portion than the portion of said main body forward of said handle portion and terminating before passing said handle portion at a stop separated from said drill bit;
    wherein said channel is adapted to receive a device in a fixed orientation relative to said drill bit;

aligning the drill bit of said surgical drill along a predetermined trajectory into a body cavity using a navigation device received into said channel of said surgical drill and retained by said sealing ring, said navigation device being tracked by a frameless navigation system and said channel being deeper than the inserted portion of said navigation device;

holding said drill bit at said predetermined trajectory; and drilling an access hole into said body cavity with said drill bit.

2. The method of claim 1, wherein said navigation device is received into a channel in said surgical drill which is on a common axis with said drill bit.

3. The method of claim 1, wherein said frameless navigation system visually tracks said navigation device.

4. The method of claim 1, wherein said access hole forms a channel along said predetermined trajectory.

5. The method of claim 1, wherein said navigation device comprises a navigation wand having an insertable portion which is inserted into said channel and tracking fiducials which retained outside of said channel.

* * * * *